United States Patent
Dao et al.

(10) Patent No.: US 7,559,915 B2
(45) Date of Patent: Jul. 14, 2009

(54) BREAST PUMP DEVICE WITH SELF-CONTAINED BREAST MILK RESERVOIR

(76) Inventors: Stella Dao, 2526 Capitol Ave., Sacramento, CA (US) 95816; Dan Garbez, 2526 Capitol Ave., Sacramento, CA (US) 95816

( * ) Notice: Subject to any disclaimer, the term of this patent is extended or adjusted under 35 U.S.C. 154(b) by 586 days.

(21) Appl. No.: 11/104,776

(22) Filed: Apr. 12, 2005

(65) Prior Publication Data
US 2008/0262420 A1 Oct. 23, 2008

Related U.S. Application Data

(60) Provisional application No. 60/618,685, filed on Oct. 13, 2004.

(51) Int. Cl.
*A61M 1/06* (2006.01)
*A41C 3/08* (2006.01)
*A61F 5/44* (2006.01)

(52) U.S. Cl. .............................. 604/74; 604/75; 604/76; 604/343; 450/36

(58) Field of Classification Search ................... 604/74; 450/36, 37; 128/846, 845; 215/11.4, 11.1; 5/632, 655, 652
See application file for complete search history.

(56) References Cited

U.S. PATENT DOCUMENTS

| | | | |
|---|---|---|---|
| 155,720 A | 10/1874 | Gray et al. | |
| 684,078 A | 10/1901 | Martin | |
| 3,840,012 A * | 10/1974 | Rushton, Jr. | 604/346 |
| 4,263,912 A * | 4/1981 | Adams | 604/75 |
| 4,270,538 A * | 6/1981 | Murphy | 604/346 |
| 4,673,388 A | 6/1987 | Schlensog et al. | |
| 4,857,051 A | 8/1989 | Larsson | |
| 4,892,517 A | 1/1990 | Yuan et al. | |
| 4,929,229 A | 5/1990 | Larsson | |
| 5,009,638 A | 4/1991 | Riedweg et al. | |
| 5,071,403 A | 12/1991 | Larsson | |
| 5,295,957 A | 3/1994 | Aida et al. | |
| 5,358,476 A | 10/1994 | Wilson | |
| 5,571,084 A * | 11/1996 | Palmer | 604/74 |
| 5,720,722 A | 2/1998 | Lockridge | |
| 5,941,847 A | 8/1999 | Huber et al. | |
| 5,954,690 A * | 9/1999 | Larsson | 604/74 |

(Continued)

OTHER PUBLICATIONS

Easy Expression Products; Easy Expression Bustier www.easyexpressionproducts.com 3pages.

(Continued)

*Primary Examiner*—Nicholas D Lucchesi
*Assistant Examiner*—Ian K Holloway
(74) *Attorney, Agent, or Firm*—Howard B. Rockman

(57) ABSTRACT

The present invention is a compact and hands-free human breast milk collection device that fits into a mother's existing nursing or standard brassiere, or in another preferred embodiment, comprises a complete nursing brassiere and milk collection system. The invention can be attached to a regular electric pump or manual pump for active milk collection and also can be used without a pump for passive milk collection. The invention comprises a breast adaptor which is preferably a funnel-shaped inlet coupled to a reservoir, wherein when the breast is inserted into the breast adaptor, the expressed breast milk is expressed into the reservoir and is stored there until the device is removed and emptied.

35 Claims, 11 Drawing Sheets

U.S. PATENT DOCUMENTS

| | | | |
|---|---|---|---|
| 6,004,186 A | 12/1999 | Penny | |
| 6,379,327 B2 * | 4/2002 | Lundy | 604/74 |
| 6,440,100 B1 | 8/2002 | Prentiss | |
| 6,575,202 B2 | 6/2003 | Lafond | |
| 6,652,484 B1 | 11/2003 | Hunckler et al. | |
| 6,706,012 B2 | 3/2004 | McKendry et al. | |
| 6,764,377 B2 | 7/2004 | Gillan | |
| 6,821,185 B1 | 11/2004 | Francis | |
| 6,866,558 B2 | 3/2005 | Luciano et al. | |
| 6,887,217 B1 | 5/2005 | Logan | |
| 6,974,361 B2 | 12/2005 | Cravaack et al. | |
| 7,094,217 B2 | 8/2006 | Fialkoff | |
| 7,128,877 B2 * | 10/2006 | Quay et al. | 422/101 |
| 7,223,255 B2 | 5/2007 | Myers et al. | |
| 2002/0193731 A1 * | 12/2002 | Myers et al. | 604/74 |
| 2003/0167037 A1 * | 9/2003 | Fialkoff | 604/74 |
| 2005/0159701 A1 * | 7/2005 | Conaway | 604/74 |
| 2006/0111664 A1 * | 5/2006 | Samson et al. | 604/74 |

OTHER PUBLICATIONS

Whisper Wear breast pump web page 2 pages www.whisperwear.com.

* cited by examiner

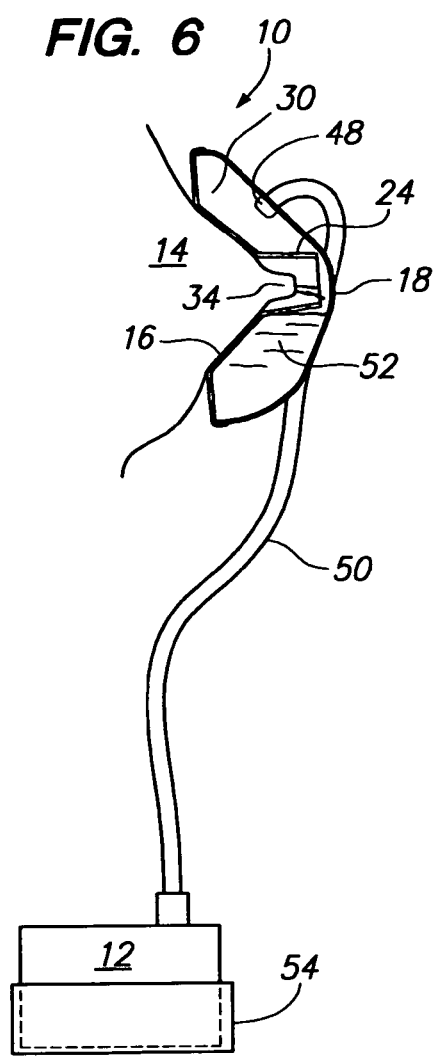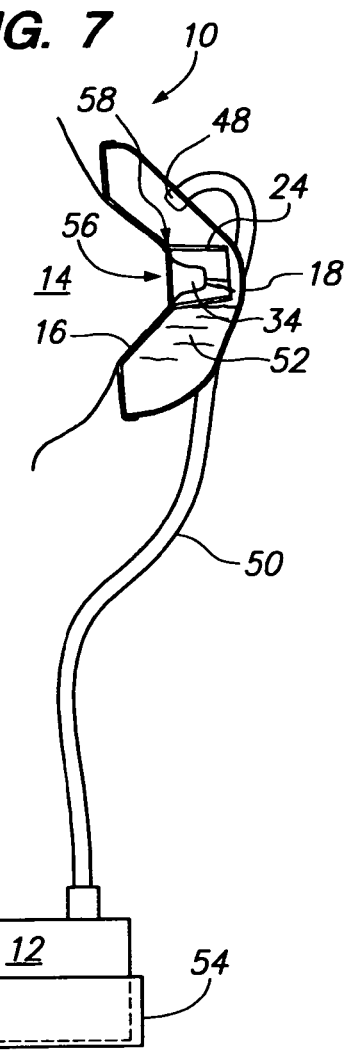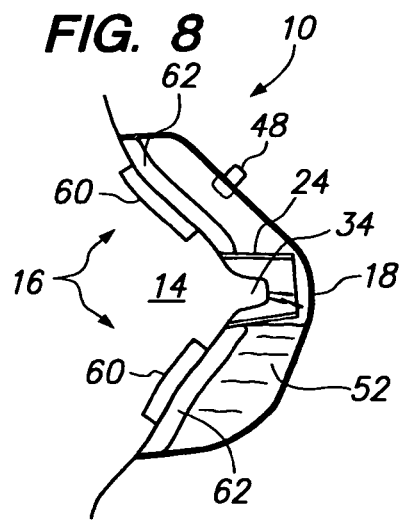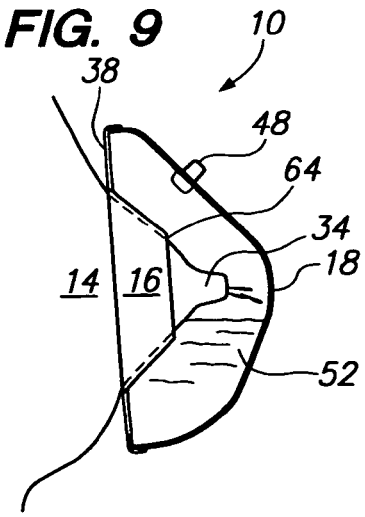

BREAST PUMP DEVICE WITH SELF-CONTAINED BREAST MILK RESERVOIR

CROSS REFERENCE TO RELATED APPLICATIONS

This utility patent application claims the benefit of U.S. Provisional Ser. No. 60/618,685 filed on Oct. 13, 2004.

TECHNICAL FIELD

This invention relates to the field of human breast milk collection devices and more specifically, to breast milk collection devices which can fit discreetly within a woman's brassiere to allow for hands-free breast milk collection.

BACKGROUND

Breastfeeding is recommended by the American Academy of Pediatrics, the World Health Organization and medical professionals worldwide as the preferred method for feeding infants during the first year of life. Human breast milk has significant health benefits that cannot be replicated by infant formula. Specifically, breastmilk has been shown to reduce the incidence of infectious diarrhea, respiratory infections, otitis media and childhood obesity. Breastfeeding has been shown to have health benefits for mothers too, by reducing the risk of postpartum bleeding and anemia. Risks are also lowered for ovarian and premenopausal breast cancer. Further, postpartum weight loss is enhanced in breastfeeding mothers. Other benefits of breastfeeding include its comforting effect upon both mother and infant. For these reasons, many health professional feel that breast feeding produces healthier, happier, infants and mothers, which is why breastfeeding is being promoted worldwide as a public health measure.

No infant formula can completely replicate the composition and benefits of human breast milk. Therefore, any proportion of breast milk in an infant's diet is preferable to no breast milk at all. Health professionals strive to encourage new mothers to provide their infants with the highest proportion of breast milk possible during the first year of life.

Unfortunately, there are many challenges to implementing breastfeeding. Breastfeeding requires constant attendance by the nursing mother every 1-2 hours, around the clock, for the baby's first 1-2 months of life, and approximately every 34 hours for the next 9 months of life. Furthermore, newborns may require up to 45 minutes per feeding. Nursing mothers must get adequate sleep, nutrition and hydration to maximize their milk production. For mothers with twins, triplets, or greater multiple births, the demand on the nursing mother's time is even greater. Some mothers have physical limitations which inhibit breastfeeding, such as inverted or sore nipples. Other mothers simply cannot make enough milk for their infants, and find that they must supplement their milk production with formula. In other cases, the physical limitations lie with the infant, namely premature or low birth weight infants who have weak suckling abilities, "floppy" infants with poor muscle tone, "tongue tied", cleft lip or cleft palate infants who cannot create a seal between their mouth and the nipple. In addition to physical limitations, societal norms create obstacles to breastfeeding. Breastfeeding in public is often prohibited, which limits mothers to breastfeeding at home.

Consequently, despite many government programs and initiatives to promote breastfeeding, most American women abandon breastfeeding long before the recommended first year of life. Studies have shown that only two-thirds of mothers breastfeed their infants when they leave the hospital, and at six months, that number shrinks to one third.

The alternatives to fulltime breastfeeding are either formula feeding, or feeding expressed human breast milk by bottle. Breast milk can be expressed, or released from the mother's lactating breasts, by massaging the breast by hand or by the application of manual or electric pumping equipment upon the breasts, both of which are commonly available in the domestic U.S. market.

In order for a woman to continue lactating a sufficient volume of milk, she must empty her breasts according to the feeding schedules and milk quantities demanded by an infant. Therefore, mothers who work outside of the home must stop working approximately every two and a half hours to pump breast milk in order to maintain an adequate milk supply. When pumping equipment is employed, it takes approximately 30 minutes for a mother to setup the pumping equipment, undress, pump, and perform cleanup. Because most current breast milk pumping and collection systems require a mother to frontally undress, a private setting is usually deemed necessary. This process, which must be continually repeated every two and a half hours is isolating, cumbersome, and extremely disruptive during work. Additionally, many breast pumping devices require the mother to use both of her hands to keep the equipment in position for efficient pumping, which prevents the mother from being able to perform other tasks as may be required in the workplace. The initial and recurring costs, involved with using pumping equipment, is a further factor which may limit the attractiveness of continuing to breastfeed.

Presently, few breast pumping devices allow for true hands-free operation. Most breast pump devices have hand-held funnel-shaped nipple adaptors, which allow suction to be applied to the nipples for milk expression. The nipple adaptors are then attached to baby bottles for milk collection. Examples of these types of devices are shown in U.S. Pat. No. 6,575,202 (Laford), U.S. Pat. No. 5,295,957 (Aida et al.), U.S. Pat. No. 5,071,403 (Larsson) and U.S. Pat. No. 5,358,476 (Wilson). Typically, suction is provided to these devices by a table-top electric pump. The pump can be situated nearby on the floor or on a tabletop, and the suction connection is made with small diameter (as little as 0.125" I.D.) flexible plastic tubing to facilitate the relatively low pressure, high volume, suction that is required to pull the woman's breast into the adapter. A typical pump that is cylinder-actuated operates as a closed system, trapping a volume of air in the adapter. When the woman's breast is pressed into the adapter, it seals itself against the sides of the adaptor and forms the enclosed space in front of the nipple. When suction is applied, the malleable breast is pulled into the adapter and toward the opening at the end of the funnel-shaped adaptor. A typical pump's cylinder, with an interior volume of several cubic inches, cycles back and forth repetitiously, completing an in-out "throw" over the course of a second or two, to create a massaging pulling rhythm upon the woman's breasts. This rhythm stimulates the mother's milk to be released, or "let-down," whereupon it flows, and is eventually collected in the manner already described. While these devices provide good suction and milk collection characteristics, hands-free operation is not possible because of the need to use the hands to hold the device against the breast during milk collection. Furthermore, because of the size and shape of these devices, the user must be frontally undressed to pump milk.

Some manufacturers have attempted to make pumping more discreet and hands-free by securing the assembly (of adaptors, bottles and hoses) with specialized straps, brassieres and harnesses. These types of devices are represented in U.S. Pat. No. 6,004,186 (Penny) and U.S. Pat. No. 6,379,327 (Lundy). However, since the entire assembly of adaptors, bottles and hoses is relatively large and cumbersome, in practice these devices still require a woman to undress in order to put on and to remove these devices with each use. Furthermore, as the bottles fill with milk, they may require some support of the bottle assembly system by hand.

U.S. Pat. No. 6,440,100 (Prentiss) presents a hands-free option which uses a low profile nipple cap held in place by a nursing brassiere. The nipple cap is placed over the nipple and a tube (for both vacuum and milk collection) extends from below the nipple cap to a collection container. A vacuum source, such as an electric pump, draws the milk from both breasts into the collection container which hangs below the brassiere. While this solution goes a long way towards providing a hands-free design, the placement of the collection container outside of the brassiere is cumbersome and unwieldy when placing and removing this device.

Also, while Prentiss attempts to provide an unobservable and virtually unnoticeable low profile application beneath normal clothing, the Prentiss design raises other issues. Namely, Prentiss attempts to minimize the profile of the nipple cap by placing the vacuum source directly below the nipple. With this design, when suction is applied, the nipple is drawn downward, which tends to inhibit the flow and expression of milk by drawing the nipple onto the vacuum source or by pinching the milk ducts. Ideally, the nipple should be drawn forward to create the smooth and unobstructed action necessary to trigger the expression of milk. Elongation of the nipple and forward suction is the same as that applied by a suckling infant. Therefore, while Prentiss is likely to be effective for passive milk collection or for women with an abundant milk supply who require little suction to release their milk, its design may result in the failure to trigger the milk expression reflex in some women.

A hands-free pump is manufactured by Whisper Wear, Inc., of Marietta Ga. This device is comprised of a dome-shaped body having a self-contained AA battery powered pump. The rear of the body has a funnel adaptor for placing the nipple. This device is only several inches in diameter and can thereby be placed easily and discreetly within a regular brassiere. A collection bag attaches to the device and hangs below the brassiere. If two devices are used at once, two bags are necessary for milk collection. While less cumbersome and completely portable when compared to the other solutions discussed herein, the use of the hanging plastic milk bags employed by the Whisper Wear device is unwieldy. Additionally, the system is expensive when the up front costs of the device are considered along with the ongoing costs of disposable batteries and single-use collection bags. This can make the system uneconomical for many mothers. But perhaps the greatest shortcoming of the Whisper Wear device when compared to the larger tabletop electric pumps is the strength of the suction it applies to the breast. The problem is one of scale. Once the Whisper Wear pump is placed over the nipple, the total volume of air trapped inside the mechanism is quite small, usually less than one cubic inch on average. Furthermore, the housing of the device limits the "throw" within this cavity to less than an inch, resulting in a much lower displacement, and therefore, a much less vigorous pumping action for milk expression. Also, being an integrated mechanical pump and battery, coupled with the weight of a suspended milk reservoir, the Whisper Wear devices are much heavier when worn hands-free within a brassiere, than the adaptor and bottle assemblies discussed previously, which use tabletop electric pumps. During use, the weight and placement of the Whisper Wear devices within the bra can pinch some milk ducts, while simultaneously emptying others. These characteristics make the Whisper Wear pump inadequate for many women as a full time pumping solution. A stronger pump is necessary for some women to relieve obstructed milk ducts and empty their breasts completely.

Therefore, it would be desirable to have a pumping system that is hands free, but that is also easy to assemble, and to position under normal clothing without the need to undress or to don complicated harness systems.

Passive milk collection is also an area of breast feeding worth addressing. Passive milk collection extends from the natural "letdown" reflex a woman experiences when an infant "latches" onto a woman's breast and begins nursing. When a breast is stimulated to release milk by a nursing infant, or through pumping a single breast, the second breast naturally begins to release milk too. If the milk being expressed from the second, unattended breast is not collected, the amount of milk that is wasted can range from a negligible percentage to as much as a third of a mother's milk supply. Therefore, due to this "letdown phenomenon" a great deal of milk that could be collected and fed to the infant via bottle is currently being wasted by most breastfeeding mothers. Presently, the predominant practice among nursing mothers to address this phenomenon is the use of absorbent, disposable or reusable pads placed inside the bra cup of the unattended breast.

Therefore, it would be desirable to have a device that can collect passively released milk from the unattended breast for subsequent feeding.

Breast feeding physically challenged infants presents its own special problems. A significant number of infants with physical challenges, such as floppy infants, premature infants, or infants with cleft lip/palate have difficulty initiating the letdown reflex on their own. These challenges may be due to a lack of adequate strength to latch onto the breast, difficulty creating sufficient suction, or a lack of focused attention. As a result, many physically challenged infants cannot derive sufficient caloric intake for their sustenance from natural breast feeding. It would therefore be desirable to have a compact, hands-free device which can be used to pump one breast, (thereby initiating the letdown reflex from both breasts), for the purpose of allowing a mother to hold and nurse a physically challenged infant from the opposite breast.

Consequently, a need exists for a breast milk collection device which can fit completely within a woman's standard brassiere. Such a device would be less likely to interfere with breastfeeding from the opposite breast and avoid the isolating, disruptive, and sometimes embarrassing need to disrobe to pump breast milk.

A need also exists for a breast milk collection device that is both powerful and hands-free.

A further need exists for a breast milk collection device that provides a viable solution for passive milk collection while simultaneously breastfeeding.

Furthermore, a need exists for a breast milk pumping and collection device which can help compromised infants breastfeed.

The foregoing reflects the state of the art of which the inventors are aware, and is tendered with a view toward discharging the inventors' acknowledged duty of candor, which may be pertinent to the patentability of the present invention. It is respectfully stipulated, however, that the foregoing discussion does not teach or render obvious, singly or when considered in combination, the inventors' claimed invention.

SUMMARY OF THE INVENTION

The present invention is a compact and hands-free human breast milk collection device that fits into a mother's existing nursing or standard brassiere. The invention can be attached to a regular electric pump or manual pump utilizing suction hoses for active milk collection and also can be used without a pump for passive milk collection.

The invention comprises a breast adaptor which is preferably a funnel-shaped inlet coupled to a reservoir, wherein when the breast is inserted into the breast adaptor, the expressed breast milk drips into the reservoir and is held there until the device is removed and emptied. In the preferred embodiment, the reservoir takes the form of a cup, and the breast adaptor takes the form of a funnel within a lid, which detachably couples upon the open end of the cup. The reservoir can also be formed into the shape of a woman's breast, thereby providing a more natural appearance when the device is placed into a woman's brassiere.

Accordingly, the following objects and advantages of the invention apply:

It is an object of this invention to provide a breast milk collection device that is hands-free, thereby allowing a mother to engage in breast milk collection while performing other daily tasks or while breastfeeding an infant on her opposite breast.

It is another object of this invention to provide a breast milk collection device that can be used with manual or electric pumps or as a passive milk collection device.

It is also an object of this invention to provide a breast milk collection device which can be placed within a woman's existing brassiere, without the need to disrobe for placement, use, or removal of the device.

Still another object of the invention is to provide a breast milk collection device which can initiate the letdown reflex from the breasts in a hands-free fashion, thereby allowing physically challenged infants to breast feed from a first breast, while collecting milk from a second breast.

Further objects and advantages of the invention will be brought out in the following portions of the specification, wherein the detailed description is for the purposes of fully disclosing preferred embodiments of the invention, without placing limitations thereon.

BRIEF DESCRIPTION OF THE DRAWINGS

The invention will be more fully understood by reference to the following drawings which are for illustrative purposes only:

FIG. 6 is a close up cutaway side view of the inventive device shown attached to a woman's breast and coupled to an electric pump device.

FIG. 7 is a close up cutaway side view of an inventive device shown attached to a breast and coupled to an electric pump device. This view also includes a milk barrier located in the breast adaptor to prevent the back flow of milk.

FIG. 8 is a close up cutaway side view of the inventive device which employs an air or fluid filled bladder for enhanced comfort and sealing characteristics.

FIG. 9 is a close up cutaway side view of the inventive device, this view eliminating the drip tube to enhance the device's usefulness for passive breast milk collection.

DETAILED DESCRIPTION OF THE PREFERRED EMBODIMENTS

The inventive device dramatically improves the feasibility of pumping breast milk for women by allowing for the use of a breast pump at a stationary place in the workplace, in a vehicle with a power adapter, or other public places with a minimum of interference or immodesty, and relatively minor disruption in these settings compared with the current state of the art for mothers who pump breast milk. Also, by eliminating the pump, the present invention can function as a passive breast milk collection device.

Figure 1:
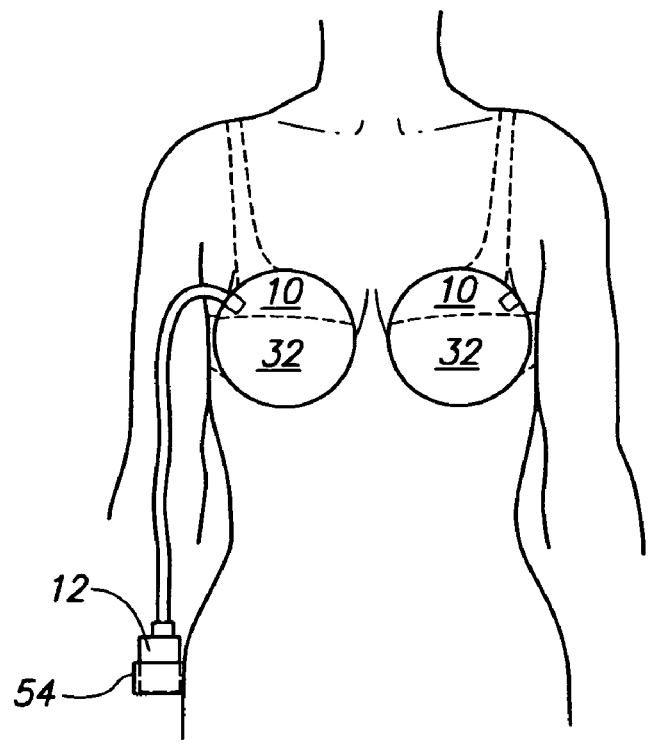
FIG. 1 is a front perspective view of a woman's torso showing the inventive device attached to each breast for completing a breast pumping cycle.
Figure 2:
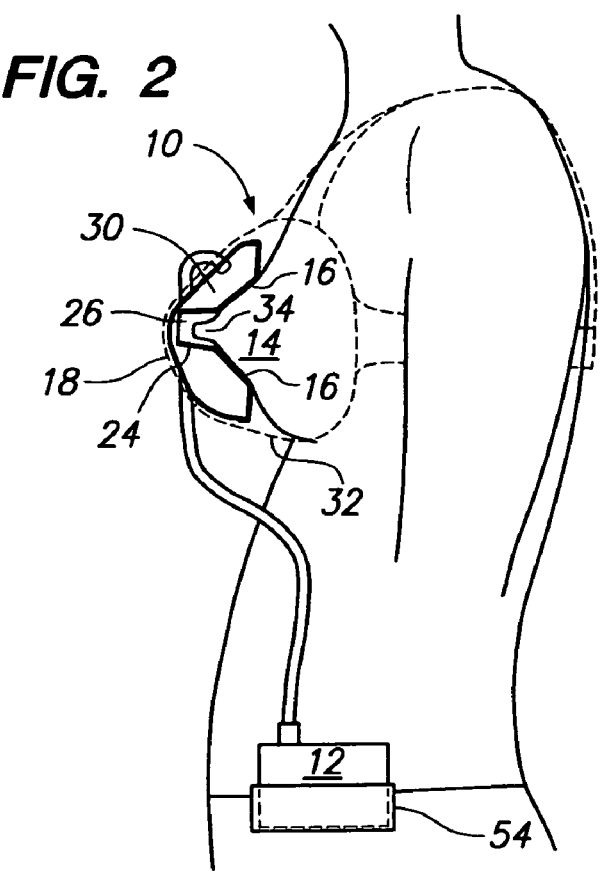
FIG. 2 is a side view of a woman's torso showing the inventive device being positioned in a brassiere for hands-free breast milk collection.

Referring to FIGS. 1 and 2, the inventive device 10 is shown attached to a woman's breast with a pump 12 attached in a typical breast milk collection mode. As shown, the device 10 includes an adaptor 16 within which the breast 14 is inserted, the adaptor 16 opening into a reservoir 18 which collects breast milk being expressed from the breast 14. The adaptor 16 includes a funnel, which is a shape that has been found to accommodate a wide variety of breast shapes and sizes. Additionally, the adaptor 16 and reservoir 18 can be made in various larger or smaller dimensions to accommodate larger or smaller breasts.

Referring also to the additional figures, the wide end of the funnel-shaped adaptor 16 opens to the rear 20 of the device 10. Proceeding forward from the rear 20 to the front 22 of the device 10, the adaptor 16 narrows and terminates at a drip tube 24 having an aperture 26 at its distal end 28, through which flows expressed breast milk to fill the reservoir 18. The funnel adaptor 16 protrudes a distance into the confines of the reservoir's interior volume 30 to give the device 10 a compact configuration. Also, the protrusion of the adaptor 16 into the reservoir 18, which can be an inch or more, gives the nipple room to elongate in a forwardly driven motion during pumping, which provides an optimal nipple orientation for milk expression. This orientation avoids pinching off of milk ducts which can lead to reduced milk expression. As shown in FIG. 2, a large portion of the breast 14 fits into the adaptor 16 and the compact configuration of the device 10 further aids in its ability to fit discreetly within a woman's standard or nursing brassiere 32. The fact that the reservoir 18 fits into a brassiere cup 32 obviates the need to have external collection bags or bottles located outside of the brassiere cup. In this way, the adaptor 16 and reservoir 18 comprise a single self-contained unit that is not dependent on external collection containers. The device 10 is shown placed within a woman's brassiere 32, in position for either pumping milk or passive milk collection. The profile of the device 10 is such that it does not protrude extensively beyond that of a normal woman's breast profile and may give the user the appearance of wearing a figure enhancing brassiere.

The adaptor 16 is preferably formed from a variety of materials including polypropylene, silicone or materials which may be developed in the future capable of making a superior seal around the breast 14 (to reduce leakage of expressed breast milk) or by making the adaptor 16 more breathable or more comfortable to wear. The materials or combination thereof can be made to be firm or soft, slick or sticky. For example, a sticky silicone might be used to form the adaptor 16 so that a tight fitting seal is made with the breast 14 while the reservoir 18 might be comprised of a rigid plastic. The rigid reservoir 18 could be formed in a shape to match that of a natural breast profile. Alternatively, the adaptor 16 and reservoir 18 might be made of a more flexible material to assume a natural breast profile as it conforms to a brassiere cup, while the drip tube 24 remains rigid to provide a closed chamber around the nipple 34 that will not collapse under the force of negative suction.

Figure 3A:
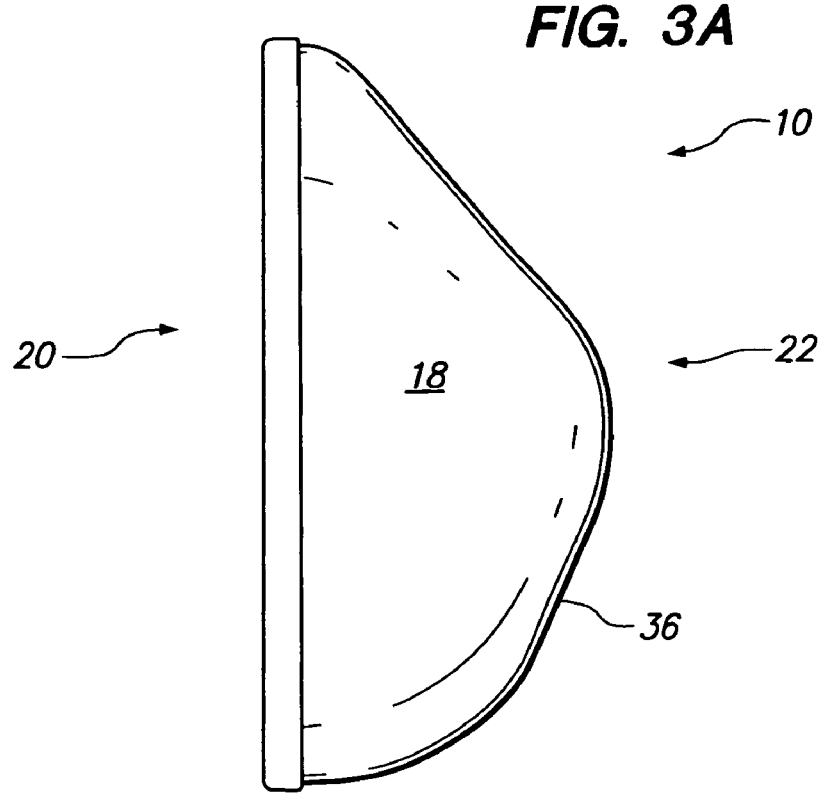
FIG. 3A is a side view of an embodiment of the inventive device which has the shape of a human breast.
Figure 3B:
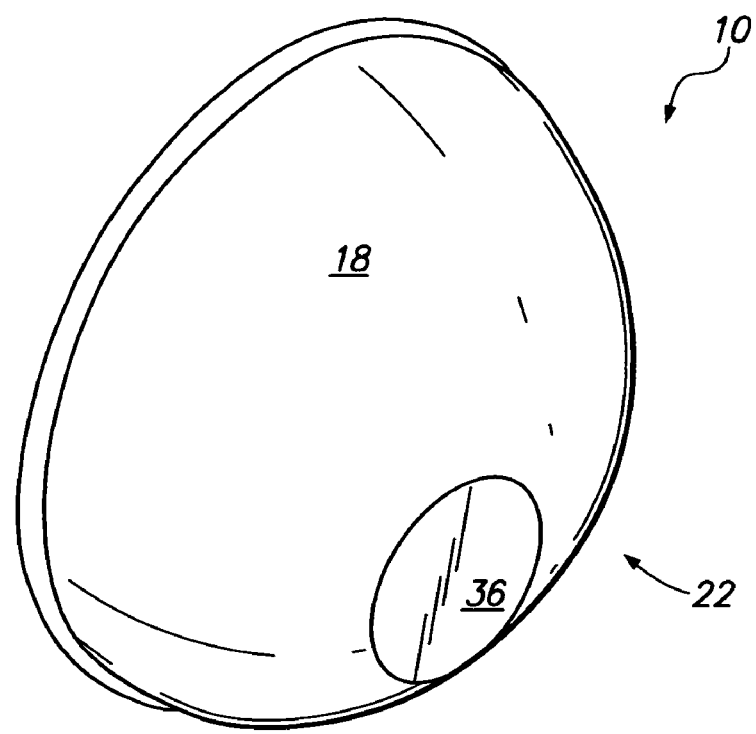
FIG. 3B is a perspective view of the embodiment of the inventive device shown in FIG. 3A.

In FIGS. 3A and 3B are shown two views of an embodiment of the device 10 which is intended to approximate the profile of a normal breast. This embodiment is shown with a flattened area 36 formed on the exterior front of the reservoir to allow the device to be set down on a flat surface, without tipping or wobbling, while containing milk. However, alternative embodiments could be made without this flattened area.

Figure 4:
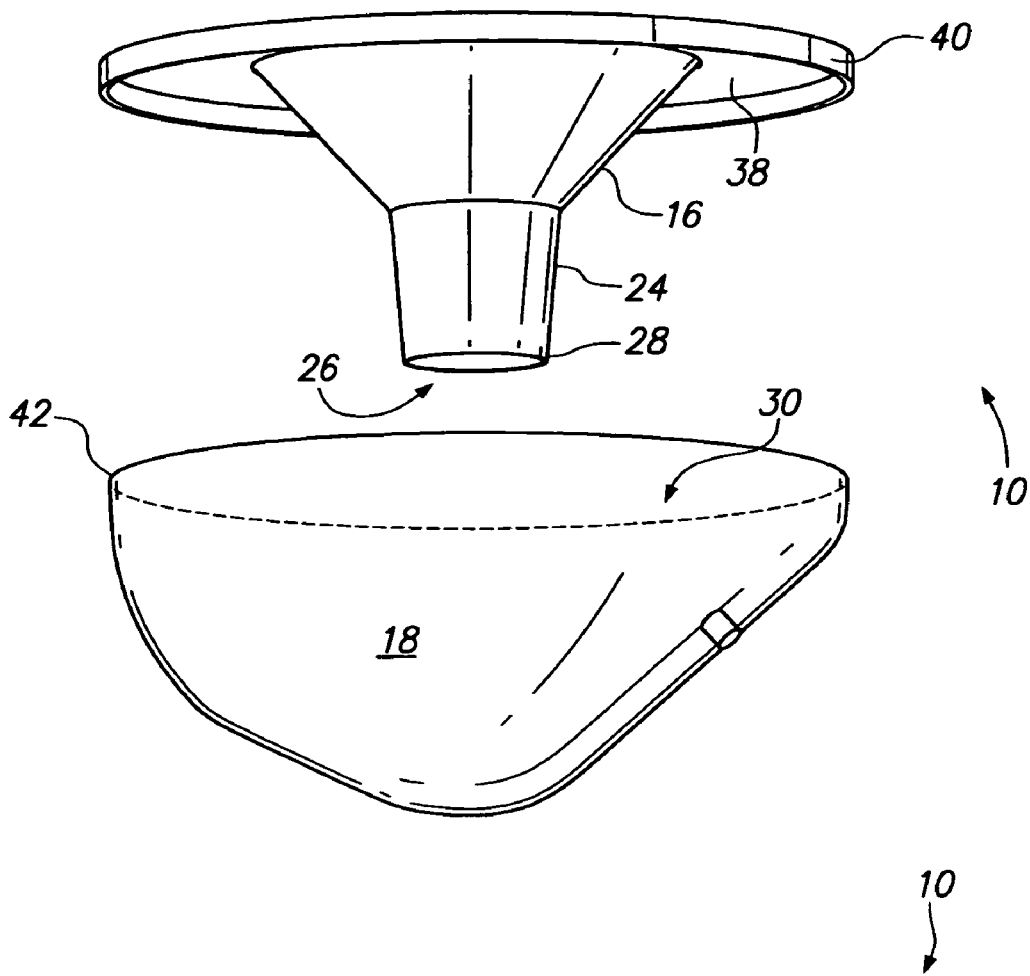
FIG. 4 is an exploded perspective view of the inventive device showing the reservoir being detachable from the adaptor.

FIG. 4 illustrates the reservoir 18 being detachable from the adaptor 16. In this fashion when the interior volume 30 of the reservoir 18 is full, the adaptor 16 can be removed and the breast milk poured into a baby bottle, or other container, for storage. In this detachable embodiment, the reservoir 18 is cup-like and the adaptor 16 functions as a lid which detachably engages with the cup-like reservoir.

Figure 5A:
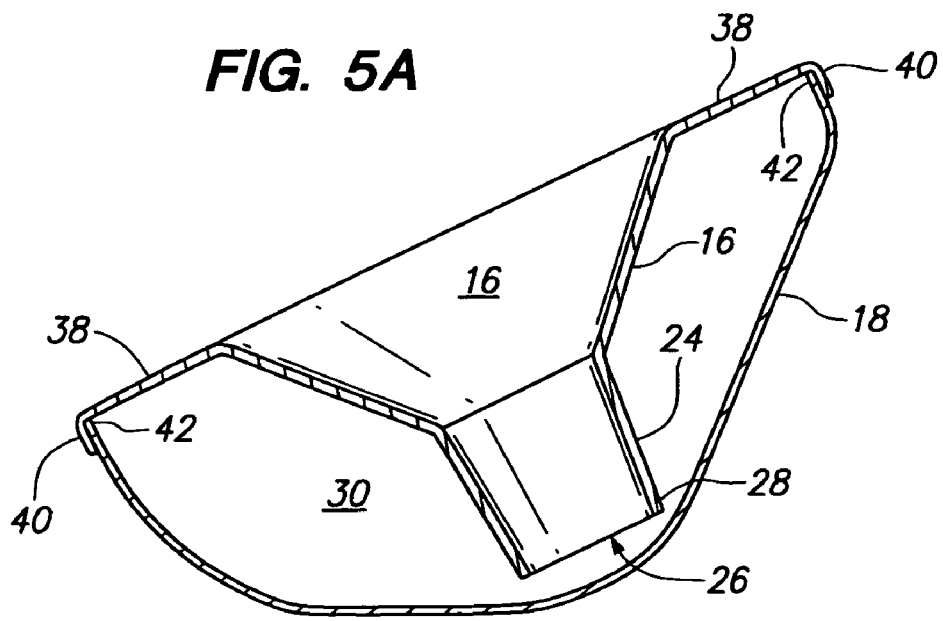
FIG. 5A is a side cutaway view of the inventive device.
Figure 5B:
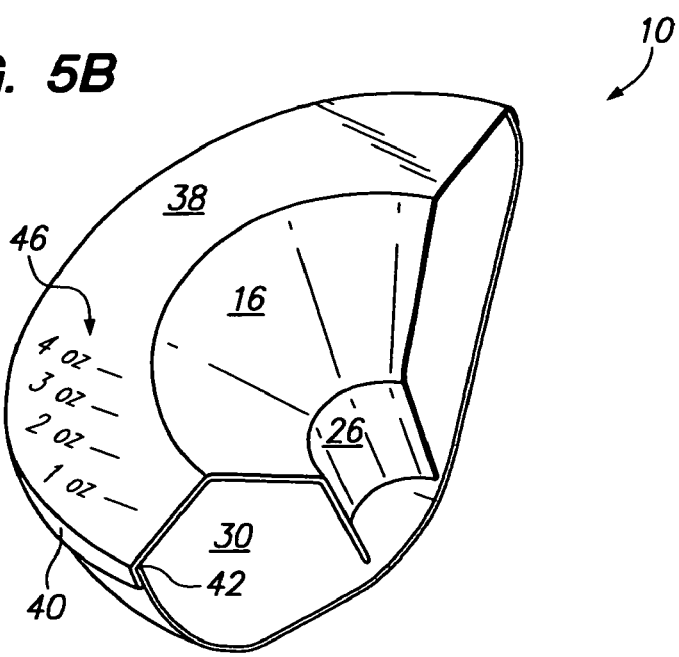
FIG. 5B is a perspective cutaway view of the inventive device.
Figure 5C:
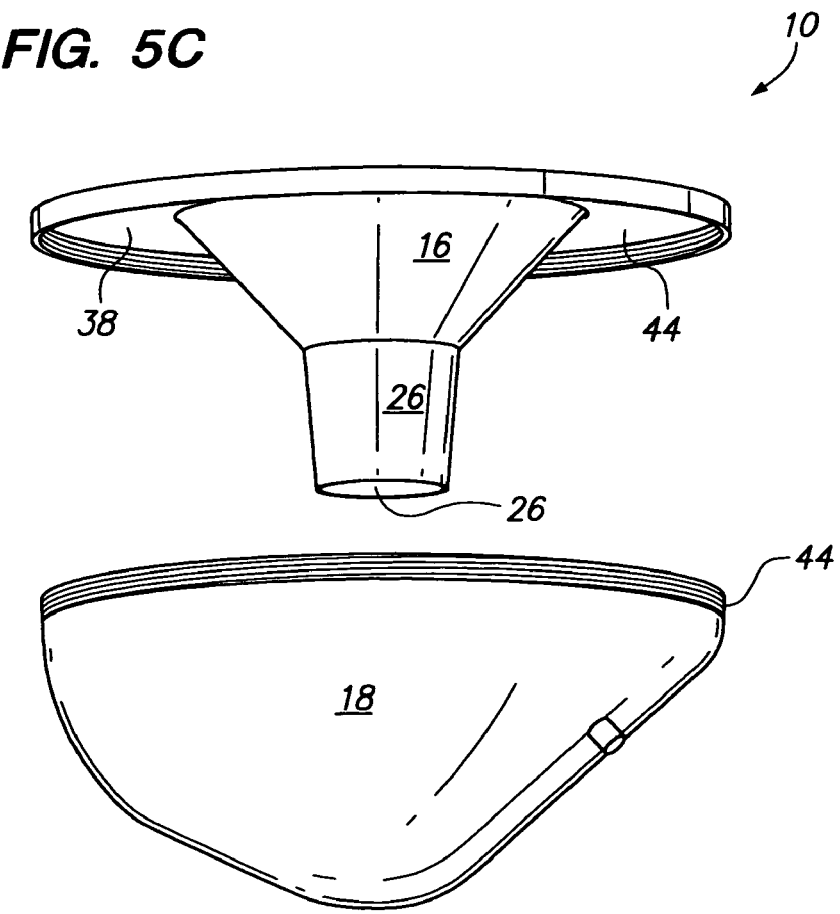
FIG. 5C is a perspective view of a screw cap embodiment of the device shown in FIGS. 5A and 5B, showing the screw cap adaptor detached from the reservoir.

Referring now to FIGS. 5A and 5B, the adaptor 16 includes a lid portion 38 which is continuous with the adaptor 16 and extends circumferentially around the cup-like reservoir 18. An overlapping lip 40 extends outward and downward from the lid portion 38 and includes a means for engaging the upper edge 42 of the reservoir 18. The engaging means can be of an overlapping snap-fit variety of a type well known in the lid fastening arts or a screw cap variety employing engaging threads 44 as shown in FIG. 5C. When attached, the adaptor 16 and reservoir 18 achieve a seal at the junction of lid portion 38 and edge 42 which cannot be compromised by the suction forces supplied by pump 12. Alternatively, the device may be one solid component, wherein the adaptor 16 does not detach from the reservoir 18 and wherein both suction and milk transfer/retrieval is accomplished through a single port hole or stem 48. Also as seen in FIG. 5B the lid portion 38 can be provided with graduations 46 denoting the number of ounces of milk contained within the reservoir 18.

FIG. 6 illustrates the inventive device 10 being used in a typical pumping cycle. A stem 48 located on the top exterior surface of reservoir 18 attaches to the pump 12 by way of a vacuum hose 50. The vacuum hose 50 attaches to the stem 48 at the top so that the pump 12 will not suction breast milk 52 into the workings of the pump 12. The pump 12 shown is a hospital grade tabletop electric pump. Additionally, although not shown, a manual pump can be employed. To further aid in the portability of the system, a belt holder 54 (See also FIGS. 1 and 2) or possibly backpack, operates to receive the electric pump 12 and allows it to be carried around while the inventive device 10 is being used. The pump 12 provides suction to the interior volume 30 of the reservoir 18 and stimulates the mother's milk to be released, or "letdown," for collection.

Examples of tabletop electric pumps presently in existence which could be used with the inventive apparatus 10 include those made by Medela, Inc., or Ameda/Hollister. These pumps can be carried in a portable manner by employing a belt holder 54 as shown in the Figures. Manual pumps which could be used include the Medela foot pump or the Versa Ped™ foot pump.

During the pumping cycle, the device 10 is located within, and supported by the brassiere (See FIGS. 1 and 2), thereby allowing the woman using the device to engage in normal workday tasks in a completely hands-free manner. A woman may use the device 10 to pump both breasts 14 at once, or else a single breast. If a woman pumps one breast 14, it is recommended that she wear the device 10 on the second breast 14 too, so that any milk 52 expressed passively, as a result of the letdown reflex, can be collected and stored.

FIG. 7 shows an alternative embodiment of the invention which is designed to further prevent leakage of expressed breast milk 52. A circular barrier 56 formed into the transition area 58 separating the narrow end of the funnel adaptor 16 and the proximal end of drip tube 24 helps prevent the backflow of expressed breast milk 52.

FIG. 8 illustrates an embodiment having the interior 60 of the funnel adaptor 16 lined with a pliable gas or liquid-filled bladder 62 for achieving enhanced sealing contact with the breast 14. The bladder 62 flexes with the shape of the breast 14 and molds the adaptor 16 thereto for enhanced sealing and comfort.

FIG. 9 shows an embodiment wherein the drip tube 24 is eliminated and, instead, the adaptor 16 narrows to an aperture 64, only, through which is placed the nipple portion 34 of the breast 14. In this version, breast milk 52 would drip directly off of the nipple 34 into the reservoir 18, without traveling down a drip tube 24. The adaptor 16 and lid portion 38 are preferably constructed from a highly flexible (possibly silicone) material which forms closely to the breast 14 to better accommodate passive breast milk collection. In addition to being used as a passive milk collector, this embodiment could also double as a false breast insert for purposes of enhancing a woman's bust line, especially if the reservoir 18 is shaped to conform to a natural breast outline.

Figure 10A:
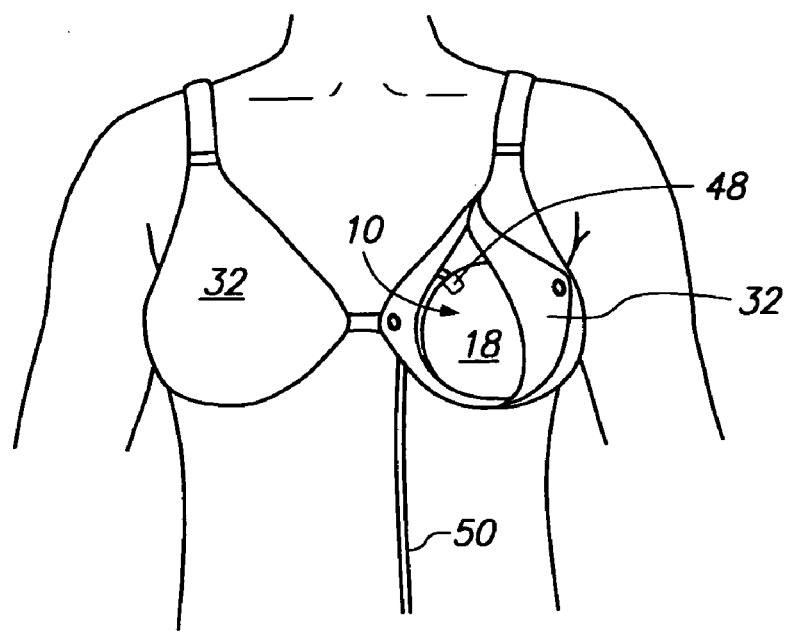
FIG. 10A is a front perspective view of a woman's torso showing the inventive device being worn in a nursing brassiere.
Figure 10B:
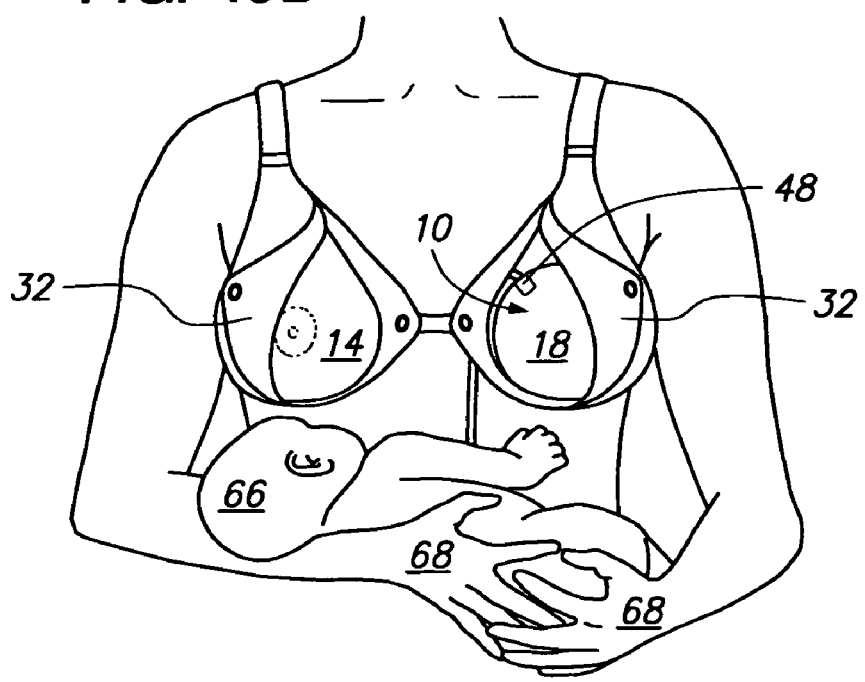
FIG. 10B is a front perspective view of a woman's torso showing the inventive device placed on the woman's left breast for milk collection while allowing her hands to remain free to nurse her infant on her opposite breast.

FIGS. 10A and 10B show the device 10 being placed within a woman's nursing brassiere 32. FIG. 10A demonstrates how such a compact device 10 may be concealed under normal clothing and used hands-free, thereby allowing a woman to carry on workplace tasks without significant interruption. FIG. 10B illustrates the hands-free advantage of the invention by showing a woman using both hands 68 to hold her nursing infant 66 on one breast 14, while either passively or actively collecting milk from the opposite breast with the device 10. Also, this illustrates how the invention can significantly simplify the nursing task for compromised infants who may nurse when the device is used with a pump on the opposite breast.

FIGS. 11A-G illustrate an alternative embodiment of the invention which introduces negative pumping pressure directly to the smaller inner sub-volume 70 of the drip tube 24 rather than to the entire reservoir volume 30 as described in the embodiments up to this point. If a similarly sized pump is used with this embodiment, the negative pressure made by the same pump is enhanced in the smaller drip tube volume 70 when compared with the previous embodiments which pump the entire reservoir volume 30. This introduction of enhanced pressure may result in faster pumping of breast milk 52 particularly in women who have difficulty with initiating the letdown reflex. Furthermore, it reduces the chances of leaking from the milk reservoir 18.

Figure 11A:
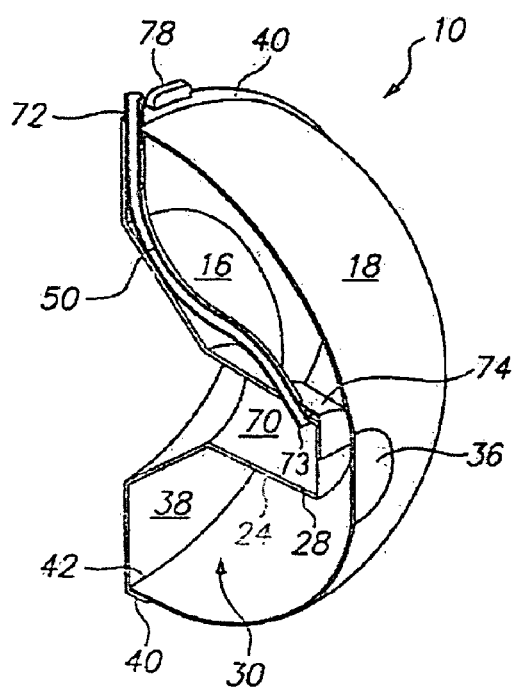
FIG. 11A is an elevated perspective cutaway view of an alternative embodiment of the inventive device which employs a valve to produce increased suction.
Figure 11B:
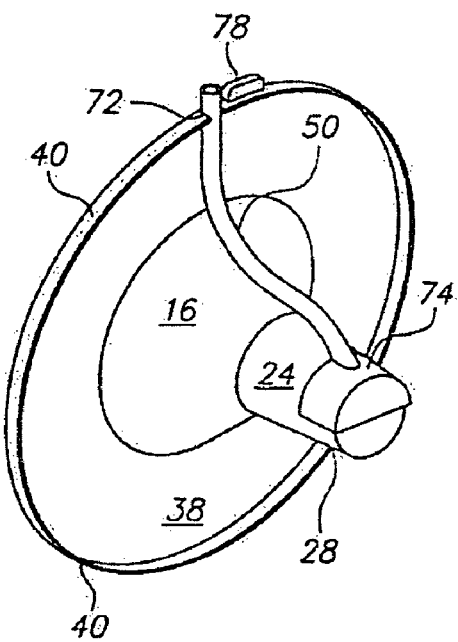
FIG. 11B is an elevated perspective view of the adaptor and valve of the embodiment of FIG. 11A shown attached to a vacuum hose.

FIG. 11A illustrates the components of the alternative embodiment 10. As shown, a vacuum hose 50 extends down through a notch 72 imparted into the lip 40 of the lid portion 38 and further extends into the drip tube volume 70 at its distal end 73. The vacuum hose 50 seats in a valve 74 which is attached to the distal end 28 of the drip tube 24. The valve seals off the drip tube volume 70 when suction is applied, while alternately allowing milk to drip through into the reservoir volume 30 when suction is released. FIG. 11B shows the adaptor 16, valve 74 and vacuum hose 50 detached from the reservoir 18. The notch 72 in the lip 40 of the adaptor 16 allows the vacuum hose 50 to be snugly seated therein. A matching notch (not shown) is placed in the edge 42 of the reservoir 18 to similarly accommodate the vacuum hose 50. When the adaptor 16 is coupled to the reservoir 18, the two notches align to form a port. At the end of the pumping cycle, the vacuum hose 50 can be removed and milk 52 poured out from the reservoir 18 through the vacuum hose port.

Figure 11C:
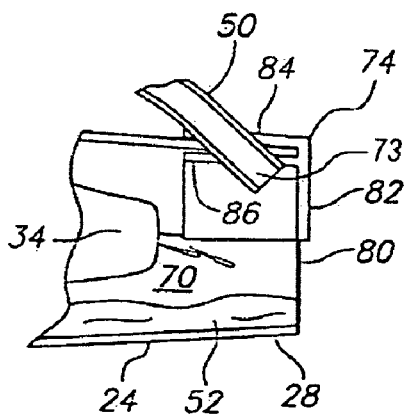
FIG. 11C is a close up side cutaway view of the drip tube, valve and distal end of the vacuum hose of the embodiment of FIG. 11A shown functioning during a negative pressure cycle.

FIG. 11C is a close up view of the drip tube 24, valve 74 and the distal end 73 of the suction hose 50 during a negative pressure cycle of the pump. With a breast 14 being inserted into the adaptor 16, the drip tube volume 70 which would be pumped is the volume extending from the front of the nipple 34 to the distal end 28 of the drip tube 24 that is closed off by valve 74. The valve 74 is preferably a flap valve having a flap 80 which seals off the distal end 28 of the drip tube 24. A barrier 76 (See FIG. 11E), which spans across the drip tube aperture 26, prevents the flap 80 from becoming suctioned inwardly into the drip tube volume 70 during the negative pressure cycle and consequently breaking suction. However, the flap valve and aperture assembly can be modified in a number of ways so that no barrier 76 is needed. Furthermore, it is conceivable to those skilled in the art, that other types of valves such as a duckbill, or a ball valve could be used in alternative embodiments.

Figure 11D:
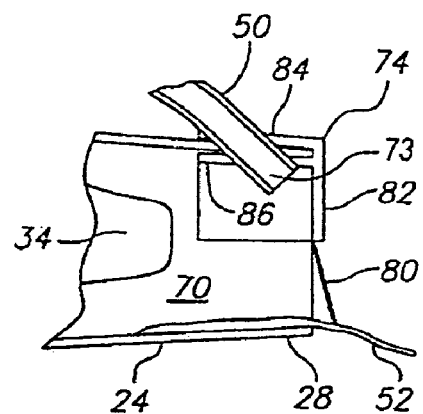
FIG. 11D is a close up side cutaway view of the drip tube, valve and distal end of the vacuum hose of the embodiment of FIG. 11A shown functioning during a positive pressure cycle.
Figure 11E:
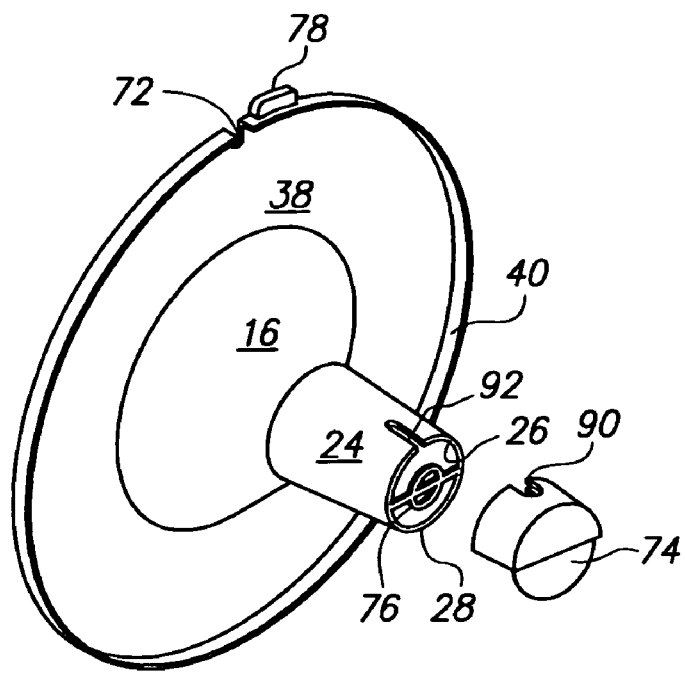
FIG. 11E is an exploded elevated perspective view of the adaptor and valve of the embodiment of FIG. 11A.
Figure 11F:
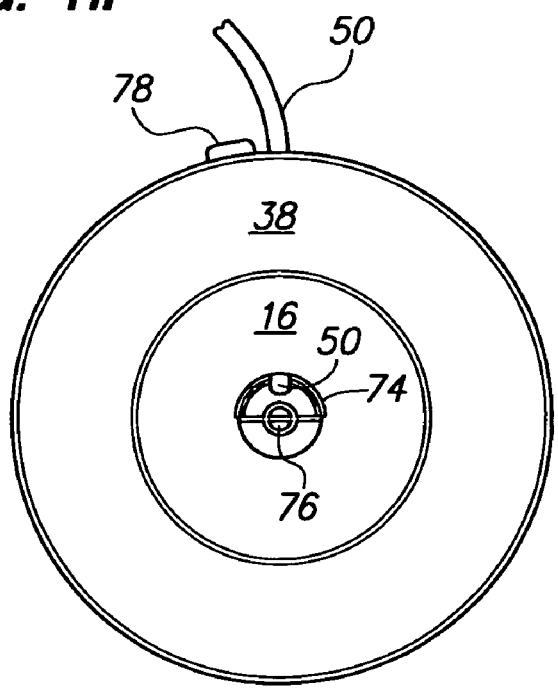
FIG. 11F is a rear view of the adaptor and valve of the embodiment of FIG. 11A.
Figure 11G:
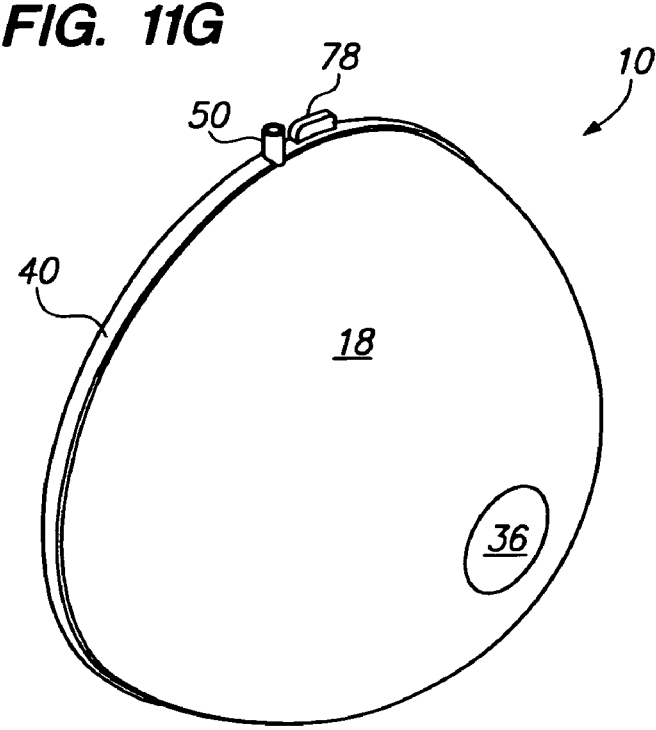
FIG. 11G is an elevated perspective view of the embodiment of FIG. 11A.

FIG. 11D shows a positive pressure cycle of the pump with the flap 80 in a relaxed state to allow the expressed milk 52 to flow into the reservoir volume 30. The barrier 76 is molded into the drip tube 24 as shown in FIG. 11E, this view showing the flap valve 74 disengaged from the end of the drip tube 24 to which it is attached. FIG. 11F illustrates another view of the adaptor 16 and barrier 76, this view showing a tab 78 molded to the lip 40 of the adaptor to allow for easy detachment of the adaptor 16 from the reservoir 18. FIG. 11G illustrates this alternative embodiment of the invention 10 fully assembled, as it might appear from the exterior.

Figure 12A:
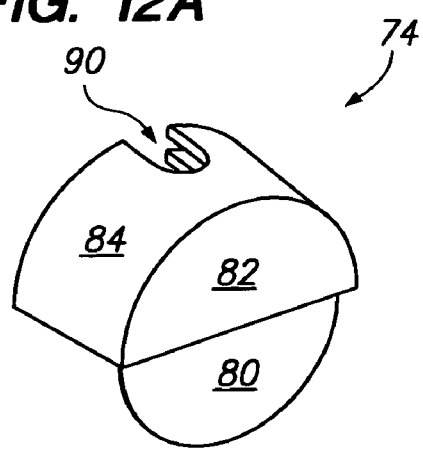
FIG. 12A is a front elevated perspective view of the flap valve component of the embodiment of FIGS. 11A-G.
Figure 12B:
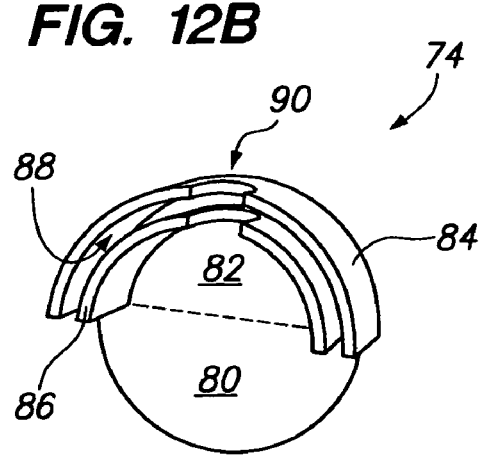
FIG. 12B is a rear perspective view of the flap valve component of the embodiment of FIGS. 11A-G.

FIGS. 12A and 12B illustrate front and rear perspective views of the preferred flap valve 74 used in the embodiment described above and shown in FIGS. 11A-G. The flap valve 74 shown is comprised of a semi-circular front face 82 from which downwardly extends the movable flap 80 shown previously in FIGS. 11C and 11D. Two stacked, semi-circular preforms 84 and 86 protrude rearward at right angles from the front face 82. The lower preform 86 has an outside circumference sized to fit snugly within the inside circumference of the drip tube 24, while the upper preform 84 has an inside circumference sized to fit snugly around the outside circumference of the drip tube 24. The space 88 located between the upper and lower preforms 84, 86 is sized to receive the distal end 28 of the drip tube 24 in the "sandwiching" manner shown in FIGS. 11C and 11D. A notch 90 is placed into each preform. The notches 90 are sized to receive the vacuum tube 50, the vacuum tube being connected to a vacuum pump as already described herein. The lower preform notch 90 is offset slightly forward of (closer to the front face 82) of upper preform notch 90, for reasons further described below. The drip tube 24 likewise has a notch 92 (See FIG. 11E) imparted inwardly from its distal end 28 for receiving the vacuum tube 50. When the flap valve 74 is installed on the distal end 28 of drip tube 24, the notches 90 of the upper and lower preforms 84, 86 of the flap valve align with the drip tube notch 92 to create a port for inserting the end of the vacuum hose 50 as shown in FIGS. 11C and 11D. As shown, the offset upper and lower notches 90 cause the vacuum hose 50 to be received into valve 74 at an angle. This angular position of the vacuum tube 50 helps prevent it from becoming disengaged from the valve 74 during pumping. The interplay of the vacuum tube 50 supplying vacuum to the inner sub-volume 70 of drip tube 24 along with flap valve 74 functioning in the manner herein described supplies an efficient and reliable mechanism for expressing milk from a woman's breast.

Figure 13A:
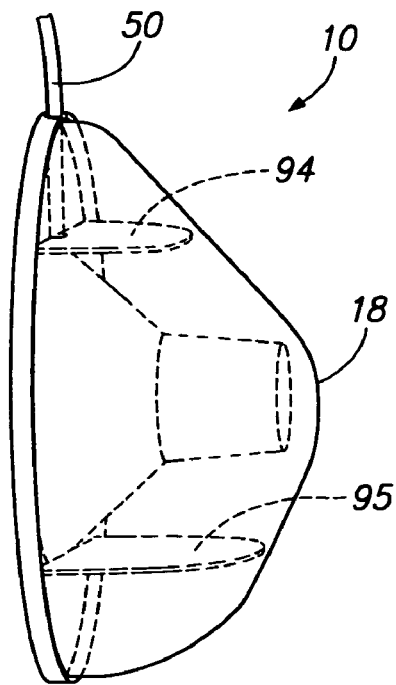
FIG. 13A is side perspective view of an alternative embodiment of the inventive device which employs baffles (shown in phantom) attached to the interior volume of the reservoir to reduce pumping volume.
Figure 13B:
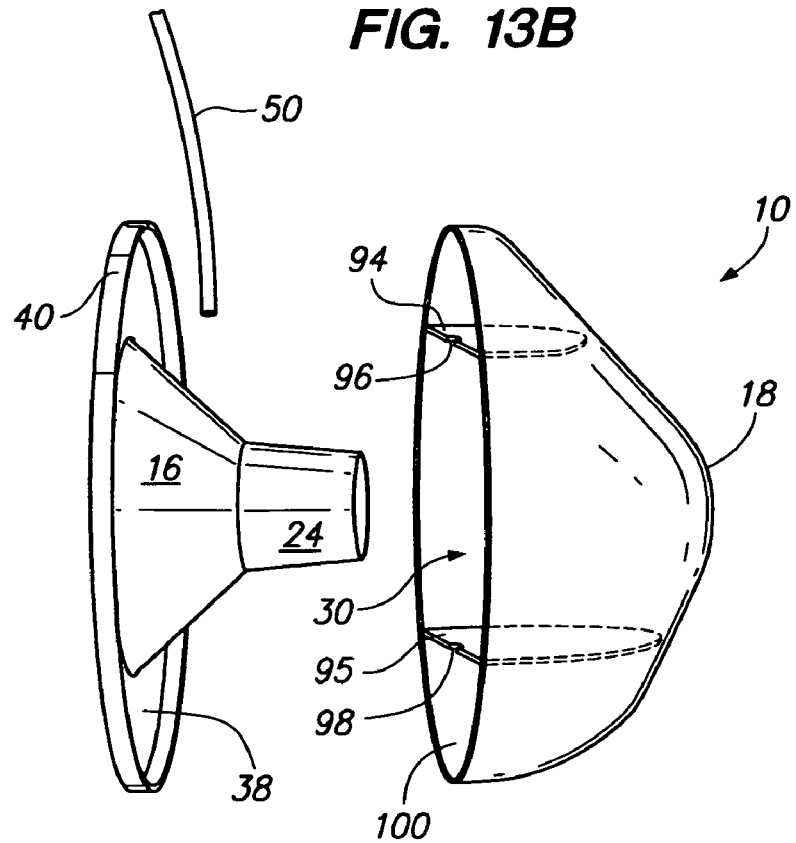
FIG. 13B is an exploded side perspective view of the embodiment shown in FIG. 13A.

FIG. 13A illustrates yet another alternative embodiment of the invention 10. This embodiment increases pumping efficiency by introducing baffles 94, 95 into the interior volume 30 of the reservoir 18. Baffles 94, 95 are attached to the interior sides of reservoir 18 and seal off a sub volume 30 between the baffles. Upper and lower baffles 94, 95 are spaced to accommodate the funnel portion of adaptor 16, there between, when the adaptor 16 is coupled to the reservoir 18 as shown in FIG. 13A. Vacuum hose 50 is introduced to the sub-volume 30 between baffles 94, 95 via notch 96 located in the upper baffle 94. The lip 40 and reservoir 18 have mating cutouts as described previously which form a port to allow entry of vacuum hose 50. The lower baffle 95 has a valve 98 to allow milk to drip into the lower portion 100 of the reservoir 18. When suction is introduced, the baffles 94, 95 reduce the interior volume 30 required to be pumped within the reservoir and a high negative pressure zone is created. If the same pump is used, the amount of suction is greater with baffles 94, 95, compared to when baffles are eliminated from the reservoir 18 (in which case the pump would be working against the entire reservoir volume 30). The advantage of this design is that fewer parts are required for assembly and cleaning.

Figure 14:
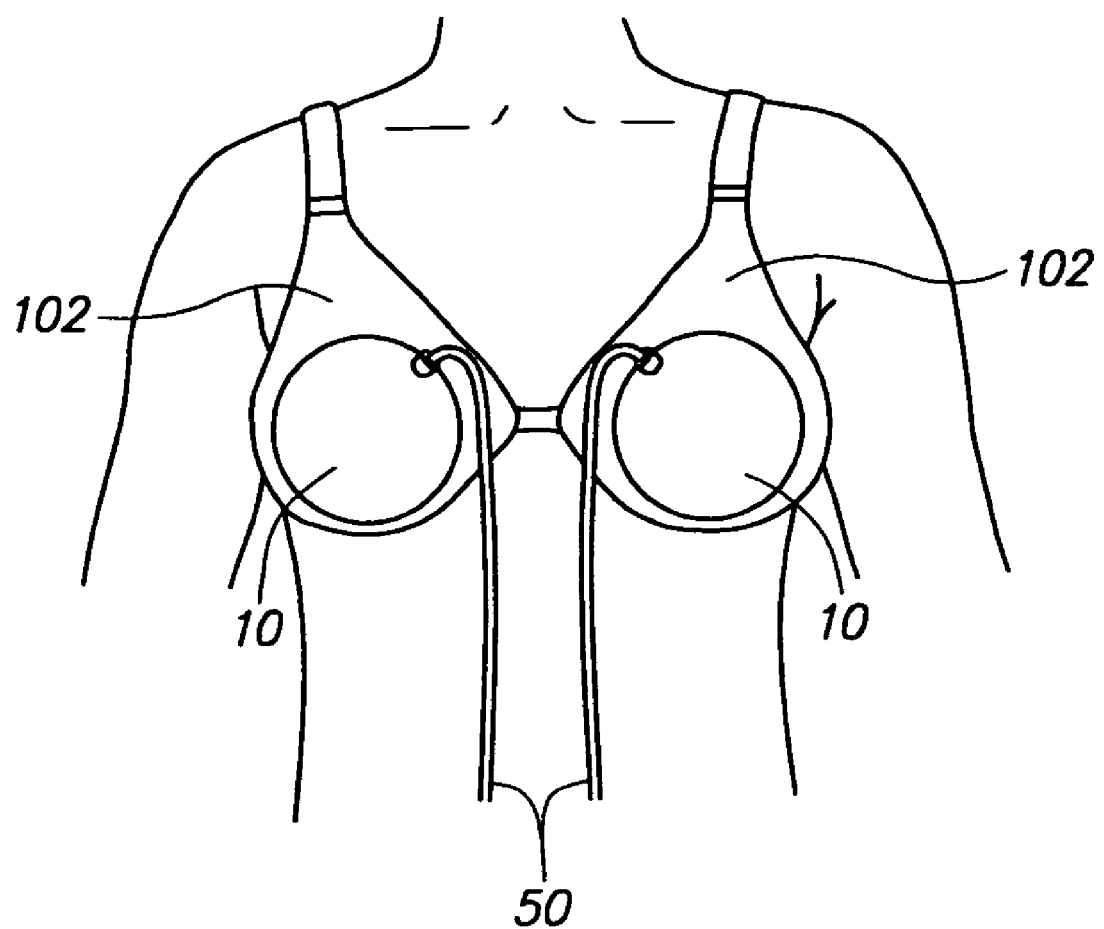
FIG. 14 is a perspective view of an alternative embodiment of the inventive device which is coupled to a suspension system, this embodiment not being dependent upon a brassiere for support upon a woman's breasts.

FIG. 14 illustrates yet another embodiment of the invention 10 which employs a system of brassiere-like adjustable straps 102 coupled to the invention 10. This allows the device to be worn like a brassiere by the wearer.

Finally, although the description above contains many specificities, these should not be construed as limiting the scope of the invention but as merely providing illustrations of some of the presently preferred embodiments of this invention. This invention may be altered and rearranged in numerous ways by one skilled in the art without departing from the coverage of any patent claims which are supported by this specification.

The invention claimed is:

1. A breast milk collection device to be secured within and supported by an ordinary or nursing brassiere worn by a lactating woman, the collection device comprising:
   a funnel shaped adaptor adapted to fittingly and sealingly receive the woman's breast;
   a reservoir having an internal volume, said internal volume adapted to collect said breast milk expressed from said woman's breast, said internal volume of said reservoir sealed against exposure to the atmosphere;
   said adaptor being received within said internal volume of said reservoir;
   said internal volume adapted to be detachably connected to an external suction source, said suction source adapted to cyclically apply a vacuum pressure to the internal volume and relieve said vacuum pressure in said internal volume,
   said cyclical application and relief of said vacuum pressure within the internal volume adapted to encourage the expression of breast milk from said breast; said reservoir adapted to allow the capture and collection of said breast milk in said reservoir.

2. The device as recited in claim 1, wherein said reservoir and said adaptor are detachably and sealingly coupled.

3. The device as recited in claim 1, wherein said internal volume is adapted to be detachably connected to said external suction source by a vacuum hose.

4. The device as recited in claim 3, wherein said external suction source is an electric pump.

5. The device as recited in claim 3, wherein said external suction source is a manually operated pump.

6. A breast milk collection device, comprising:
   a funnel shaped breast adaptor adapted to receive a woman's breast therein;
   a reservoir receiving said breast adaptor within an internal volume of said reservoir, said internal volume of said reservoir sealed against exposure to the atmosphere, said reservoir being sealingly attached to said breast adaptor, said reservoir adapted to receive breast milk produced from said woman's breast seated in said breast adaptor;
   said internal volume adapted to be detachably connected to an external suction source, said suction source adapted to cyclically apply a vacuum pressure to the internal volume and relieve said vacuum pressure in said internal volume, said cyclical application and relief of said vacuum pressure adapted to encourage the expression of breast milk from said breast;
   said reservoir adapted to allow the capture and collection of said breast milk in said reservoir.

7. The device as recited in claim 6, wherein said external suction source is an electric pump.

8. The device as recited in claim 6, wherein said external suction source is a manually operated pump.

9. The device as recited in claim 6, further comprising a brassiere for fittingly positioning said device therein, said brassiere selected from the group consisting of an ordinary brassiere and a nursing brassiere.

10. The device as recited in claim 6, further comprising means adapted to hold and support said collection device in a fitting and sealing manner against said woman's breast.

11. A breast milk collection device, comprising:
    a funnel shaped breast adaptor, said breast adaptor adapted to receive a woman's breast therein;
    a reservoir, said reservoir having an internal volume, said internal volume adapted to receive and store breast milk produced from said woman's breast seated in said breast adaptor;
    said breast adaptor and said reservoir forming a single unit adapted to fit within said woman's brassiere; and
    said internal volume adapted to communicate with an external suction source, said external suction source adapted to cyclically provide suction force to said internal volume of said reservoir and relieving the suction force in the internal volume of said reservoir.

12. The device as recited in claim 11, wherein said breast adaptor is adapted to sealingly attach to said woman's breast to form a suction seal.

13. The device as recited in claim 11, further comprising a brassiere for fittingly positioning said device in said brassiere.

14. A breast milk collection device, comprising:
    a funnel having a wide receiving end adapted to receive a woman's breast therein and a narrow end opposite said receiving end, said narrow end including an aperture adapted to receive the nipple portion of said breast there through;
    a reservoir enclosing said funnel to form a single unit with said funnel, said reservoir sealed against exposure to the atmosphere, wherein an internal volume of said reservoir is adapted to receive breast milk through said aperture of said narrow end of said funnel;
    said internal volume adapted to be detachably connected to an external suction source, said suction source adapted to cyclically apply a vacuum pressure to the internal volume and relieve said vacuum pressure in said internal volume; and
    said cyclical application and relief of said vacuum pressure adapted to encourage the expression of breast milk from said breast;
    said reservoir adapted to allow the capture and collection of said breast milk in said reservoir.

15. A breast milk collection device, comprising:
    a funnel having a wide end adapted to receive a woman's breast therein and a narrow end opposite said receiving end, said narrow end tapering into a drip tube, said drip tube extending forwardly from said narrow end, said drip tube terminating at its distal end, said distal end having an aperture;
    a reservoir enclosing said funnel therein to form a single unit with said funnel, wherein an internal volume of said reservoir is adapted to receive breast milk through said aperture of said drip tube;

said internal volume adapted to be detachably connected to an external suction source, said suction source adapted to cyclically apply a vacuum pressure to the internal volume and relieve said vacuum pressure in said internal volume; and said cyclical application and relief of said vacuum pressure adapted to encourage the expression of breast milk from said breast;

said reservoir adapted to allow the capture and collection of said breast milk in said reservoir.

16. A breast milk collection device, comprising:

a funnel having a wide end adapted to receive a woman's breast therein and a narrow end opposite said receiving end, said narrow end tapering into a non-collapsible drip tube, said drip tube extending forwardly from said narrow end, said drip tube terminating at its distal end, said distal end having an aperture, said drip tube capable of resisting collapse under the force of negative suction pressure;

a reservoir enclosing said funnel therein to form a single unit with said funnel, wherein an internal volume of said reservoir is adapted to receive breast milk through said aperture of said drip tube;

a reduced volume within said reservoir, said reduced volume adapted to be detachably connected to an external suction source, said reduced volume formed within said drip tube, said suction source adapted to cyclically apply a vacuum pressure to said reduced volume and relieve said vacuum pressure in said reduced volume;

said cyclical application and relief of said vacuum pressure adapted to encourage the expression of breast milk from said breast;

said cyclical relieving of said vacuum pressure in said reduced volume adapted to allow the capture and collection of said breast milk in said reservoir; and a valve attached to said distal end of said drip tube, said valve closing off said aperture and creating said reduced volume within said drip tube, said reduced volume cyclically becoming a high negative pressure zone upon introducing the external source of suction to said reduced volume, said high negative pressure zone adapted to encourage the expression of breast milk from said woman's breast.

17. The device as recited in claim 16, wherein said valve is a flap valve.

18. The device as recited in claim 15 wherein said reservoir further comprises an exterior surface shaped to approximate the contour of a woman's breast.

19. The device as recited in claim 15, further comprising means for attaching said external source of suction pressure to a reduced volume within said drip tube.

20. The device as recited in claim 19, wherein said means for attaching said external source of suction pressure is a vacuum hose.

21. The device as recited in claim 20 wherein said external suction source is an electric pump.

22. The device as recited in claim 20 wherein said external suction source is a manually operated pump.

23. The device as recited in claim 15, wherein said reservoir further comprises a baffle system, said baffle system forming a sub volume within said internal volume of said reservoir, said sub volume forming a high negative pressure zone upon the introduction of said external suction source to said sub volume.

24. The device as recited in claim 15, further comprising a detachable closure for detaching said reservoir from said funnel.

25. The device as recited in claim 24, wherein said detachable closure remains fast upon application of adequate positive and negative pressure to said device.

26. The device as recited in claim 15, wherein said funnel is made of a flexible material, said funnel further comprising a pliable fluid filled bladder lining an interior of said flexible funnel, said bladder adapted to mold said flexible funnel to comfortably and sealingly receive said woman's breast.

27. The device as recited in claim 15, further comprising a barrier located at a transition area separating said narrow end of said funnel and a proximal end of said drip tube.

28. The device as recited in claim 14, further comprising a belt holder adapted to support said external suction source upon the waist of a wearer.

29. The device as recited in claim 1, wherein said reservoir has a circumferential edge, said circumferential edge detachably engaging said adaptor.

30. The breast milk collection device of claim 1, wherein:
said adaptor and said reservoir comprise a single self contained unit adapted to collect said milk.

31. The breast milk collection device of claim 30, wherein:
said adaptor forms a wall of said reservoir.

32. The breast milk collection device of claim 30, wherein:
said adaptor includes a lid portion continuous with the adaptor;
said lid portion extending circumferentially around and engaging an edge of said reservoir.

33. The breast milk collection device of claim 32 wherein:
said lid portion has a surface facing said internal volume of said reservoir;
said surface of said lid portion forming a wall of said internal volume of said reservoir.

34. A breast milk collection device to be secured within and supported by an ordinary or nursing brassiere worn by a lactating woman, the collection device comprising:

a funnel shaped adaptor adapted to fittingly and sealingly receive the woman's breast, said adaptor having a wide receiving end adapted to receive said woman's breast and a narrow end opposite said wide receiving end, said narrow end including an aperture adapted to receive the nipple portion of said breast;

a reservoir having an internal volume, said internal volume adapted to collect said breast milk expressed from said woman's breast, said reservoir detachably engaged to said adaptor; and said internal volume adapted to be detachably connected to an external suction source, said suction source adapted to cyclically apply a vacuum pressure to the internal volume and relieve said vacuum pressure in said internal volume;

said cyclical application and relief of said vacuum pressure adapted to encourage the expression of breast milk from said breast;

said reservoir adapted to allow the capture and collection of said breast milk in said reservoir.

35. The breast milk collection device of claim 34 wherein:
said adaptor and said reservoir comprise a single self contained unit adapted to collect and store said milk.

* * * * *